United States Patent [19]

Seo

[11] 4,191,193
[45] Mar. 4, 1980

[54] CATHETER HEAD-TYPE TRANSDUCER

[75] Inventor: Iwao Seo, Ibaragi, Japan

[73] Assignee: Mitsubishi Petrochemical Co. Ltd., Chiyoda, Japan

[21] Appl. No.: 770,782

[22] Filed: Feb. 22, 1977

[30] Foreign Application Priority Data

Feb. 29, 1976 [JP] Japan .................. 51/021431

[51] Int. Cl.$^2$ .............................................. A61B 5/02
[52] U.S. Cl. ................... 128/675; 252/62.9; 73/727
[58] Field of Search ............. 128/2.05 E, 2.05 P, 128/2.05 F, 2.05 D, 675; 307/88 ET; 179/111 ET, 100.41 B; 29/592 E; 252/62.9 E

[56] References Cited

U.S. PATENT DOCUMENTS

| | | | |
|---|---|---|---|
| 3,553,625 | 1/1971 | Stedman | 128/2.05 E |
| 3,607,754 | 9/1971 | Asahina et al. | 307/88 ET X |
| 3,858,307 | 1/1975 | Yoshimura et al. | 307/88 ET X |
| 3,970,862 | 7/1976 | Edelman et al. | 29/592 X |
| 3,971,250 | 7/1976 | Taylor | 307/88 ET X |
| 3,996,922 | 12/1976 | Basham | 128/DIG. 29 X |

FOREIGN PATENT DOCUMENTS

| | | | |
|---|---|---|---|
| 2231491 | 1/1973 | Fed. Rep. of Germany | 128/2.05 E |
| 51-1039 | 1/1976 | Japan | 252/62.9 R |
| 51-7498 | 7/1976 | Japan | 252/69.9 R |
| 51-23698 | 2/1976 | Japan | 252/62.9 R |
| 51-25800 | 3/1976 | Japan | 252/62.9 R |
| 51-31892 | 3/1976 | Japan | 252/62.9 R |
| 51-31894 | 3/1976 | Japan | 252/62.9 |
| 51-31895 | 3/1976 | Japan | 252/62.9 |
| 51-36597 | 3/1976 | Japan | 252/62.9 |
| 442788 | 1/1972 | U.S.S.R. | 128/2.05 E |

OTHER PUBLICATIONS

"Catheter Pressure Transducers," Millar Instrument Catalog, Millar Instruments, Inc., Houston, Tex. (prior to 2/29/76).

Primary Examiner—Robert W. Michell
Assistant Examiner—Francis J. Jaworski

[57] ABSTRACT

A catheter having a transducer that comprises an organic high polymer filmlike piezoelectric element or elements. The catheter has the capacity of converting, safely and with accurate wave shapes, pressure in the living body, for example blood pressure, pressure in a thorax, or intrauterine pressure, into an electric signal. By means of this catheter, pressure in the living body can be measured.

8 Claims, 15 Drawing Figures

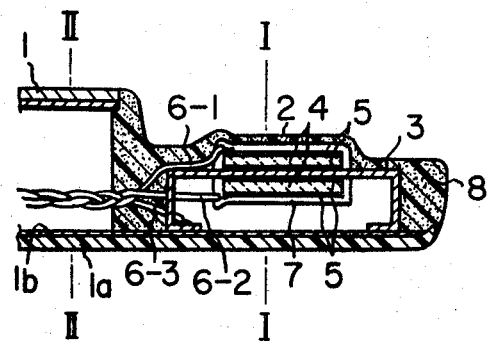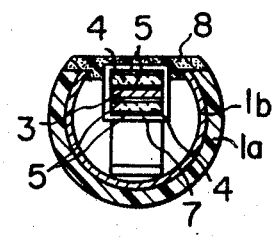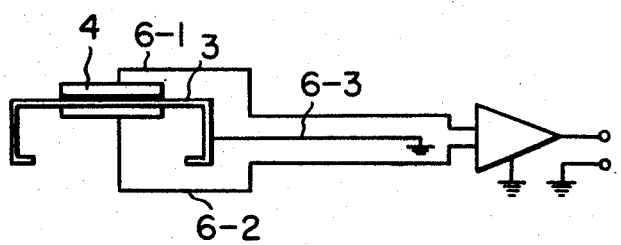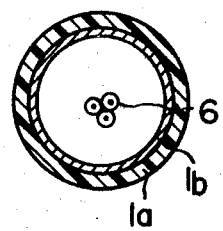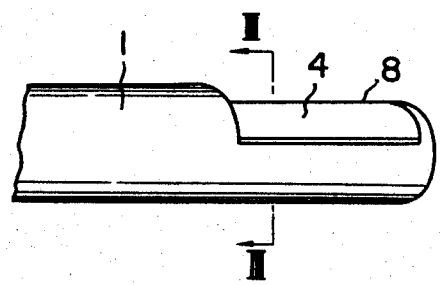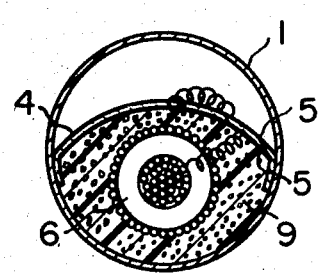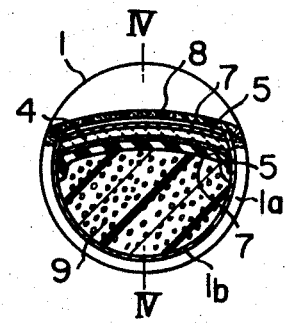

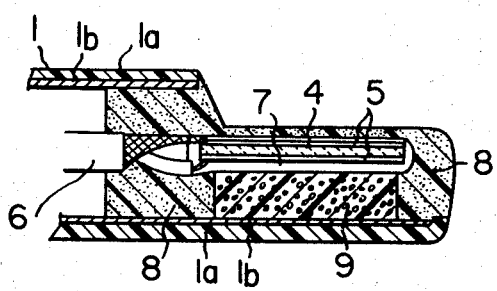
FIG. 8
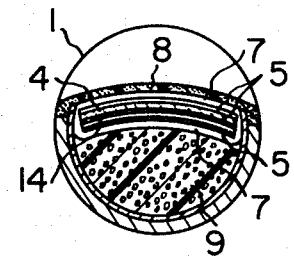
FIG. 9
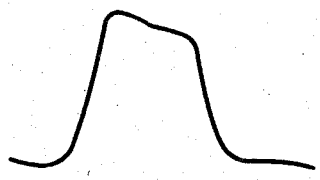
FIG. 10(a)
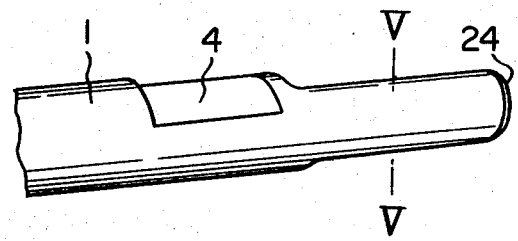
FIG. 11
FIG. 10(b)
FIG. 12
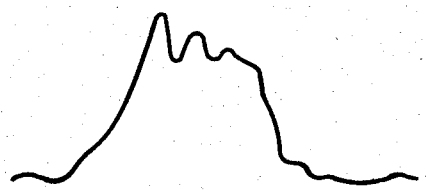
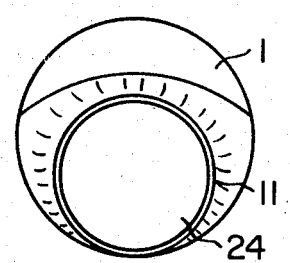
FIG. 13
FIG. 14
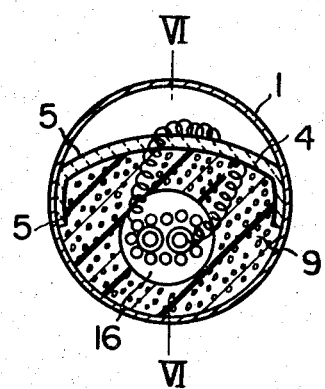
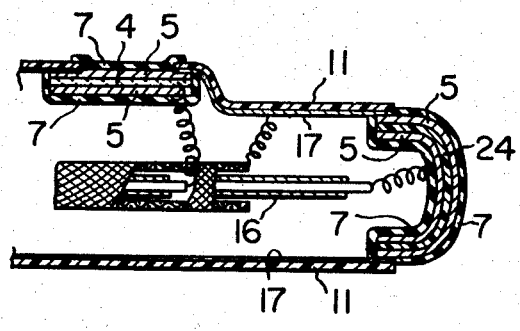

CATHETER HEAD-TYPE TRANSDUCER

BACKGROUND OF THE INVENTION

The present invention relates to a catheter having transducer which comprises an organic high polymer filmlike piezoelectric element or elements.

With the use of this invention, a filmlike piezoelectric element with excellent pliability can be mounted on a catheter tip, whereby pressure in the living body such as blood pressure, pressure in a thorax, or intrauterine pressure, can be detected directly and read-out as an electronic signal. From the resulting signal wave shapes, a diagnosis can be made.

Also, with this invention the catheter can be provided with two filmlike piezoelectric elements with excellent pliability. These can be mounted on the catheter head and on the catheter side wall, whereby pressure waves at two different points can be detected and read-out as electronic signals corresponding to the pressure waves by the two piezoelectric elements, so that the flow rate of blood can be measured from a time lag between two pressure waves.

In the prior art, for example for measuring pressure in the heart's blood vessel, a catheter connected to an electronic tonometer has been used. A catheter (i.e., a tubule of plastic resin such as fluoride resin, polyurethane, polyethylene, etc.) filled with physiological saline solution is inserted in the blood vessel. Through this catheter the blood pressure existing at the catheter tip is transmitted outside the body, and this pressure is converted into an electronic signal by an electronic tonometer. Wave shapes of this blood pressure are analysed, and from this information, diagnosis is made, and circulation of the blood is analyzed. The foregoing is known prior art.

However, in this prior art method, a real zero point cannot be determined because a difference of water pressure exists between the catheter tip and the transducer (electronic tonometer). Also there are influences such as diminution of pressure, delay of pressure changes due to the visoelasticity of saline, and other physical effects, as the pressure wave at the catheter tip is transmitted to the electronic tonometer through the saline solution. Therefore, accurate measurements cannot be obtained in the above prior art method.

In recent years, a method has become known for solving the above problems, which method is, however, still under study. In this newer and known method, a semiconductor strain gage is mounted on a catheter tip where it will function as a pressure transducer, and the catheter is inserted in the blood vessel or in the living body so that the transducer is placed in the vicinity of the point in the blood vessel or in the body where the pressure measurement is to be made. Measurement is made by the strain gage. Pressure which is applied on this transducer can be converted into electronic signal which is recorded by a recorder.

In this latter method, when the strain gage is used as a pressure transducer, voltage is applied to the strain gage at the catheter tip. Therefore measurement in this method involves the risk that a short-circuit or leak would occur in the human body and inflict an injury upon a person. Furthermore, this latter method has the following defects: the structure of the transducer is intricate, it withstands mechanical impact poorly, and is fragile. Also, clinical application as a catheter is restricted because pliability of the catheter tip is lost by the transducer. Furthermore operation is difficult, because a semiconductor strain gage has a great temperature drift.

The following features are desirable for a transducer to be used in a living body:
(1) that the transducer does not have the above defects;
(2) that sensitivity, stability, and responsiveness are excellent;
(3) that the working range is wide;
(4) that environmental disturbance is small;
(5) that it is easy to insert it into the measured living body and its influence on the living body is minimal;
(6) that it is small-sized; and,
(7) that it is possible to sterilize it.

BRIEF SUMMARY OF THE INVENTION

The object of the present invention is to provide a catheter which carried on its head a filmlike piezoelectric element with excellent pliability which satisfies the above conditions and functions as a pressure transducer.

Other and further objects, features and advantages of the invention will appear more fully in the following description.

BRIEF DESCRIPTION OF THE DRAWINGS

In the drawings:

FIG. 1 is a vertical sectional view of a top part of a first embodiment of the present invention;

FIG. 2 is a cross-sectional view taken on line I—I of FIG. 1;

FIG. 3 is a cross-sectional view taken on line II—II of FIG. 1;

FIG. 4 is a wiring diagram of the embodiment of FIG. 1;

FIG. 5 is a perspective illustration of the principal part of the second embodiment of the present invention;

FIG. 6 is a explanatory cross-sectional view for explaining internal structure of the second embodiment of the present invention;

FIG. 7 is a cross-sectional view taken on line III—III of FIG. 5;

FIG. 8 is a cross-sectional view taken on line IV—IV of FIG. 7;

FIG. 9 is a cross-sectional view of a modified embodiment of the present invention in which a compensating electrode is provided;

FIGS. 10(a) and (b) are graphical representation of wave shapes of electrical tracings of pressure the left ventrical in the heart;

FIG. 11 is a perspective illustration of the principal part of the third embodiment of the present invention;

FIG. 12 is a view from the distal end of the catheter of FIG. 1;

FIG. 13 is a explanatory cross-sectional view on line V—V of FIG. 11 for explaining internal structure; and FIG. 14 is a longitudinal sectional view taken on line VI—VI of FIG. 13.

DETAILED DESCRIPTION

Referring to the attached drawings, in FIGS. 1 to 4 inclusive, there is shown the first embodiment of the present invention.

In the drawings, numeral 1 designates a catheter pipe or tubule, which consists of soft material. It is generally round so that a transducer 2 mounted on the tip of the catheter can be inserted into the body to a point where the pressure is to be measured. Generally, the catheter tubule consists of plastic as fluoride resin, polyethylene, polyurethane, polyvinyl chloride, etc., and is molded in the shape of a pipe. In the example of a catheter for the examination of the heart (cardiovascular), the outside diameter thereof is from 1 to 3 mm, for example 2.67 mm, and the inside diameter is from 0.56 to 2.08 mm, for example 1.55 mm, and the length is from 50 to 125 cm. In the example of a catheter for the examination of the system, the outside diameter of the catheter is from 1.98 to 9.9 mm, for example 4.62 mm and the length is 40 cm.

Inside of outer wall 1a of the catheter tubule 1; a relatively undeformable inner wall 1b consisting of tubular polyester fabric or stainless steel braid is usually inserted so that the outer wall 1a is protected from being crushed, and the catheter head can assuredly be turned by rotating the tube for controlling the direction of the catheter when the catheter is inserted in living body. The transducer 2 is constructed as a bimorph in which filmlike piezoelectric elements 4 and 4 are adhered to a shim 3.

Shim 3 will be made of material which has high elasticity and small strain, for instance, thin rectangular plates of 20 to 500μ in thickness of phosphor bronze, copper, or stainless steel, for example.

Material, form, and size of shim 3 can be determined by considering gains of the transducer and its frequency characteristic.

Electrodes 5 and 5 on both surfaces thereof are adhered to both sides of each of the piezoelectric elements. Opposing sides are of the same pole, preferably of the negative pole.

Film like piezoelectric elements 4 and 4 are made up of organic high polymer piezoelectric material which is an electret of high polymer material or which is an electret of a composite consisting of high polymer resin and piezoelectric ceramics.

As filmlike piezolelectric elements in this invention, pliable piezoelectric material which has an elastic modulus below $1 \times 10^{11}$ dyne/cm$^2$, preferably below $5 \times 10^{10}$ dyne/cm$^2$, can be employed.

Filmlike piezoelectric elements can be used in the form of electrets obtained by a manufacturing method which comprises stretching films of thermoplastics such as polyvinyl fluoride, polyvinylidene fluoride, polyvinyl chloride, polyacrylonitrile, polycarbonate, etc., by several times their original length while at a temperature near the softening temperature, forming electrodes 5 on both surfaces of the resulting stretched films either by evaporation of silver or aluminium or by chemical plating, the heating from room temperature to the temperature near the softening point being accomplished under a condition of applied electric field of 100 to 700 KV/cm DC, and then cooling the product.

Alternatively, as filmlike piezoelectric element, suitable electrets can be obtained by manufacturing a composite which comprises mixing from 90 to 10% by volume of piezoelectric ceramics with from 10 to 90% by volume thermoplastic resin. Said thermoplastic resin is a crystalline and polar resin such as polyacetal, vinylidene fluoride resin, or polyamide. Alternatively, said electrets can be obtained by manufacturing a composite which comprises mixing from 90 to 10% by volume piezoelectric ceramics with from 10 to 90% by volume of a blend polymer. Said blend polymer is obtained by blending 99 to 20% by weight of said thermoplastic resin and 1 to 80% by weight of a polar polymer such as chloroprene rubber, acrylonitrile-butadiene rubber, epichlorohydrin rubber, chlorinated polyethylene, urethane rubber. Then the resulting composite is molded into a film of 5–500μ thickness. The molded composite is heated from 40° C. to 100° C. after forming metal layers on its opposite sides by evaporating or plating silver or aluminium, and applying thereto an electric field of direct current above 50. Thereafter the molded composite is cooled.

For piezoelectric ceramics, ceramics in which domain-switching is possible can be employed among ferroelectric substances. The following such materials are known:

(1) Single component; $BaTiO_3$, $PbTiO_3$, etc.
(2) Two component; $PbTiO_3$-$PbZrO_3$, $PbTiO_3$-$Pb(Zn_{1/3}Nb_{2/3})O_3$, etc.
(3) Three component; $PbTiO_3$-$PbZrO_3$-$Pb(Mg_{1/3}Nb_{2/3})O_3$, etc.

Further as typical ceramics, lead zirconate-lead titanate solid solution ceramics or barium titanate ceramics can be used.

A typical filmlike piezoelectric element can be obtained by a manufacturing method which comprises adding from 10 to 90 percent by volume the thermoplastic resin to lead zirconate-lead titanate solid solution ceramics or barium titanate ceramics of about 0.2 to 45μ particle diameter, molding the resulting composite, forming the electrodes on both surfaces thereof, and electretizing the resulting molded composite. The filmlike piezoelectric element is cut into the size of 1.5 mm in width by 6 mm in length, and the cut filmlike of piezoelectric elements 4 and 4 are adhered with opposing sides of the same pole, to both surfaces of shim 3 with adhesive. Thereafter as shown in FIG. 4, ends of cables 6-1, 6-2 and 6-3 are respectively connected with two filmlike piezoelectric elements 4, 4 and shim 3.

Because the high polymer piezoelectric element is thermolabile, connection should be accomplished at room temperature, for example, by electro-conductive adhesive or by ultrasonic seal.

The other side, connection of the cable to shim 3 can be done by soldering, if preferred.

As cables 6-1, 6-2 and 6-3, can be bundles of three wires twisted together, each wire being made of seven silver fibers of 0.076 mm diameter, and insulated by fluoride resin of 0.025 mm thickness.

The surface of bimorph type transducer 2 is coated with insulating material 7 of high resistance and waterproofing, so as to be insulated. Thereafter, cables 6-1, 6-2 and 6-3 are inserted into the catheter tubule 1. Then feet of shim 3 are fixed with adhesive on the inner surface of the catheter tubule in the vicinity of the catheter tip to secure and raise the piezoelectric elements from the inner surface. An electrical connector (not shown) is provided at the ends of cables 6-1, 6-2, 6-3.

Then the surrounding space in the catheter tubule is filled up with filler material 8 for encapsulating transducer 2. Optionally, a thrombus inhibiter such as physiological silicone coating may be coated on surface thereof.

A bimorph-type transducer has the advantages that sensitivity of the transducer is raised, and noise caused by outer turbulence, temperature drift, and induced current of cable, is eliminated.

However, the transducer can instead be consistituted by a single filmlike piezoelectric element and still provide important advantages of the invention.

For insulating material 7, α-cyano-acrylate adhesive (trade name: Aron Alpha A "Sankyo" manufactured by Sankyo Co., Ltd.), polyurethane resin, polyolefin resin, silicon resin, polysulfone resin, epoxy resin, and alkyd resin can be employed. For insulating material 7, one having volume resistivity above $10^{10}$ Ωcm is desirable.

For filling material 8, epoxy resin, silicone resin, polyurethane resin, polysulfone resin, α-cyano-acrylate adhesive, etc., can be employed.

In FIGS. 5 to 8 inclusive, there is shown a second embodiment of the present. In this embodiment, the catheter is constituted by single piezoelectric film.

In the drawings, numeral 1 designates a catheter tubule (diameter: about 3 mm) and length of 1.2 m, which has pliability and whose tip is cut round so as to be easily inserted in the living body. Numeral 4 designates a filmlike piezoelectric element which is attached to the tip of catheter tubule 1 by silicone adhesive. Numerals 5, 5 designate electrodes which are mounted on both sides of the filmlike piezoelectric element 4 by a vacuum evaporation method. Numeral 6 designates low noise cable which connects electrodes 5, 5 of the filmlike piezoelectric body to measuring equipment (not shown). For example, a coaxial cable sheather with outer braid can be employed for cable 6. Especially low noise cable in which shield effect is improved by an intervening semiconductor layer consisting of plastics and carbon powder mixed therewith between inner insulating layer and braid. Herein, the exposed surface of electrodes 5 of piezoelectric body 4 is coated with insulating material 7. Numeral 9 designates an elastic body filling space cathether tubule 1 and filmlike piezoelectric element 4. The elastic body serves as material for giving an appropriate tension to the filmlike piezoelectric element 4. The elastic body 9 also serves as material for fixing cable 6.

For the elastic body 9, elastomeric plastics and foam plastics such as polyurethane resin, silicone resin, epoxy resin, etc., can be used. Polyurethane resin which can be injected as a liquid to foam and harden in place is preferred.

A filmlike piezoelectric element 4 for use in the second embodiment can be manufactured by the following method. Aluminum electrodes are formed on both surfaces of uni-axially oriented polyvinylidene fluoride film of 20μ in thickness by a vacuum evaporation method, and the film with the electrodes is kept at 130° C. in a constant temperature box and to the film electric field of direct current of 600 KV/cm is applied for an hour. As the result, piezoelectric body of electric constant $d_{31} = 16 \times 10^{-12}$ C/N was obtained.

In FIGS. 5 through 8, a filmlike piezoelectric element with thickness of 20μ and with area of 2 mm by 5 mm is mounted in such a way that the stretching direction goes with the traversing direction of a catheter. Numeral 8 denotes a cover.

Because the transducer of the second embodiment has the above structure, the transducer at a tip of catheter can be inserted in the blood vessel (vascular), and for example, can be introduced into the inside of the heart. Then blood pressure of the heart can be converted into electric signal by a transducer comprising the filmlike piezoelectric element 4, and the electric signal can be sent outside the human body through cable 6, and blood pressure of the heart can be measured by means of appropriate measuring equipment, for example an oscillograph. FIG. 10(a) shows wave shapes of pressure in the left ventricle of the heart which was measured by the transducer of the first embodiment while FIG. 10(b) shows pressure which was measured by a conventional electric tonometer (prior art) employing physiological saline, and wherein noise caused by resonance of catheter is contained.

In the event wave shapes are disordered by moving of cathether, measuring can be done as follows. A piezoelectric element 14 for compensation is mounted as shown in FIG. 9 and any difference of electric signals between piezoelectric element 4 and piezoelectric element 14 is extracted. Noise is cancelled by the compensation signal.

In FIGS. 11 to 14 inclusive, there is shown a third embodiment of the present invention.

In the third embodiment, filmlike piezoelectric elements 4 and 24 are mounted on the side wall of catheter tubule 1 and on the head of catheter tubule 1, respectively. The third embodiment is constructed so as to be able to measure the flow rate of blood as well as wave shapes of blood pressure at the same time.

Herein, two core shield cable 16 can be employed so as to send electric signals which occur in piezoelectric elements 4 and 24 outside the human body. Numeral 11 designates a thin part of head of a catheter tubule 1. The inside of the thin part of head of the catheter is metal-plated, and the metallic film 17 inside the catheter is connected electrically to both an electrode 5 of piezoelectric element 24 and to shield braid of the cable 16. The metallic film 17 inside the catheter has a shielding effect. The surface of electrode 5 is coated by insulating material 7 similar to the second embodiment and further may be coated by silicone in order to prevent thrombus.

Filmlike piezoelectric elements 4 and 24 which can be employed in the third embodiment can be manufactured by the following method. With polyacetal resin (trade name: Delrin 500, manufactured by du Pont Company, Ltd.), chlorinated polyethylene with chlorine content of 30 percent by weight was mixed with the component ratio of 60/40 (polyacetal resin/chlorinated polyethylene) percent by weight. Then, with the resulting blend polymer, lead zirconate-lead titanate solid solution ceramics powder is mixed with the component ratio of 50/50 percent by volume. Then, the resulting composites is molded into a film. On both surfaces of the resulting film, silver is evaporated to form electrodes. The resulting film with electrodes is kept at 80° C. in a constant temperature box and to the film electric field of direct current of 300 KV/cm is applied for an hour. As a result, a filmlike piezoelectric element is obtained which has excellent pliability and excellent moldability and large piezoelectricity of piezoelectric constant $d_{31} = 35 \times 10^{-12}$ C/N.

The filmlike piezoelectric element does not have anisotropy. Therefore, the filmlike piezoelectric element can be formed in shape of sphere as filmlike piezoelectric element 24 on catheter heads shown in FIGS. 11 to 14 so as to minimize its influence on the living body.

However, filmlike piezoelectric elements being used in the present invention are not limited to those of the embodiments. Constructions of a transducer for use in the present invention is also not limited to those of the embodiments.

As is apparent from the above detailed description, in the present invention, because a very pliable filmlike piezoelectric element is employed, a transducer according to the present invention has excellent sensitivity, stability, responsibility, safety, etc., and can be small-sized. Pliability of the catheter tip is not diminished at all. The structure thereof is simple, and strong against an external force such as impact, and handling thereof is easy. Furthermore in the transducer according to the present invention x-ray detection of position of the transducer in the cardiovascular system, where the transducer is introduced into the blood vessel, can be done by lead contained in the cable or dispersed in the filmlike piezoelectric element without using material for detection. As described above, the transducer according to the present invention has very notable effects.

What is claimed is:

1. A catheter comprising a tube having a length and a tip, and a transducer on said tip which is comprised of a pair of organic high polymer filmlike piezoelectric elements being mounted on each opposite face of a rectangular shim having feet at each end fixed to and raising the piezoelectric elements from a relatively undeformable inner wall of the catheter tube so that said piezoelectric elements are centrally distorted in response to fluid pressure exerted on said tip, said shim being fixed to the inner wall of the catheter tube at the catheter tip, said piezoelectric elements being adhered to said shim with opposing sides of the same pole to said shim, and conductor means comprising a cable connected respectively with both piezoelectric elements and said shim extending through said tube to conduct the electrical signal generated by the transducer to means for receiving it.

2. A catheter as claimed in claim 1, wherein said piezoelectric elements are from the group consisting of from 10 to 90 percent by volume polyacetal, polyamids or polyvinylidene fluoride and from 90 to 10 percent by volume piezoelectric ceramics, and electretized.

3. A catheter as claimed in claim 1, wherein said piezoelectric element or elements are from the group consisting of piezoelectric material which comprises a composite of blend polymer resin and piezoelectric ceramics, the blend polymer resin being from the group consisting of from 99 to 20 percent by weight polyacetal, polyamide or polyvinylidene fluoride and from 1 to 80 percent by weight polar polymer, the blend polymer resin being added to the piezoelectric ceramics so that amount of the blend polymer is from 10 to 90 percent by volume, the composite being molded and electretized.

4. A catheter as claimed in claim 1, wherein said piezoelectric element consist of stretched polyvinylidene fluoride electretized by electric field.

5. A catheter as claimed in claim 1, wherein said transducer is a bimorph-type.

6. A catheter according to claim 1, wherein said shim is a thin plate of 20 to 500μ in thickness from the group consisting of phosphor bronze, copper, or stainless steel.

7. A catheter as claimed in claim 1, wherein said piezoelectric element is made from the group consisting of from 10 to 90 percent by volume polyacetal, polyamide or polyvinylindene flouride and from 90 to 10 percent by volume piezoelectric ceramics, and electretized.

8. A catheter as claimed in claim 1, wherein said piezoelectric element is made of blend polymer resin and piezoelectric ceramics, said blend polymer resin consisting of 99 to 20 percent by weight polyacetal resin and from 1 to 80 percent by weight polar polymer, said blend polymer resin being added to the piezoelectric ceramic so that the amount of the blend polymer is from 10 to 90 percent by volume, the composite being molded to film and electretized.

* * * * *